United States Patent [19]

Herman

[11] Patent Number: 5,093,326

[45] Date of Patent: Mar. 3, 1992

[54] REPELLANT COMPOSITIONS

[76] Inventor: Stephen Herman, 9341 Hazel Cir., Villa Park, Calif. 92667

[21] Appl. No.: 369,678

[22] Filed: Jun. 19, 1989

[51] Int. Cl.⁵ ................. A01N 43/26; A01N 37/02; A01N 31/00

[52] U.S. Cl. .................. 514/172; 514/463; 514/546; 514/724; 514/918; 514/919

[58] Field of Search ............. 514/557, 558, 560, 724, 514/918, 919, 546; 549/431; 424/DIG. 10

[56] References Cited

U.S. PATENT DOCUMENTS

| | | | |
|---|---|---|---|
| 925,590 | 6/1909 | Neel | 549/431 |
| 1,210,949 | 1/1917 | Knox | 549/431 |
| 1,910,564 | 5/1933 | Rankin | 549/431 |
| 2,083,572 | 6/1937 | McKee et al. | 424/613 |
| 2,243,053 | 5/1941 | Ramage | 568/959 |
| 2,356,062 | 8/1944 | Johnson | 260/410.7 |
| 2,750,411 | 6/1956 | Fisher et al. | 562/505 |
| 3,360,472 | 12/1967 | Renold | 252/186.26 |
| 3,504,038 | 3/1970 | Beal | 568/469 |
| 4,451,480 | 5/1984 | DeVillez | 514/859 |
| 4,591,602 | 5/1986 | DeVillez | 514/463 |
| 4,632,980 | 12/1986 | Zee et al. | 530/380 |

FOREIGN PATENT DOCUMENTS 27371 11/1912 United Kingdom .
787748 12/1957 United Kingdom .

OTHER PUBLICATIONS

Powers et al., *Vet Hum Toxicol*, vol. (30)3, pp. 206–210, 1988.

Second College Edition: The American Heritage Dictionary.
Chemical Abstracts (104:143994d), 1988.
Sharma et al., J. Med. Ent., vol. 11:617–621 (1974).
P. Bailey et al., "Complexes and Radicals Produced during Oxonation of Olefins", *Ozone Reactions with Organic Compounds, Advances in Chemistry*, Series 112, pp. 1–8 (1972).
R. Murray et al., "Ozonolysis: Formation of Cross Diperoxides", *Ozone Reactions with Organic Compounds, Advances in Chemistry*, Series 112, pp. 9–21 (1972).
Criegee and Korber, "Fragmentation of Ozonides by Solvents", *Ozone Reactions with Organic Compounds, Advances in Chemistry*, Series 112, pp. 23–24 (1972).

*Primary Examiner*—Frederick E. Waddell
*Assistant Examiner*—Kevin Weddington
*Attorney, Agent, or Firm*—Knobbe, Martens, Olson & Bear

[57] ABSTRACT

Insecticidal and repellent compositions comprising ozonides of hydrocarbons are disclosed. Hydrocarbons which are believed to be active when prepared in accordance with the present invention include terpenes and unsaturated fatty acids derived from plant and animal sources. Other examples of suitable unsaturated hydrocarbons include natural and synthetic steroids, alkenes and their substituted derivatives, and other naturally or synthetically unsaturated hydrocarbons derived primarily from petroleum. Methods of use for the compositions are also disclosed.

18 Claims, No Drawings

REPELLANT COMPOSITIONS

BACKGROUND OF THE INVENTION

This invention relates to ozonides of unsaturated hydrocarbons. More particularly, it relates to the use of these trioxyacyclopentanes in insecticidal and repellent preparations.

Procedures for preparing ozonides of oil-soluble compounds are known in the art, being disclosed, for example, in U.S. Pat. No. 925,590 to Neel, U.S. Pat. No. 2,083,572 to McKee, and U.S. Pat. No. 4,451,480 to De Villez.

The prior art discloses that some particular types of ozonide structures have certain pharmacological activity. For example, in U.S. Pat. No. 925,590, Neel discloses the use of ozonides for inhalation therapy, because it was believed to have a therapeutic effect for consumption and asthma. Knox, U.S. Pat. No. 1,210,949 discloses ozonation of castor oil in order to produce a germicidal laxative. Johnson, U.S. Pat. No. 2,356,062 discloses the use of ozonides of glycerine trioleates for external application, because it was believed that those particular triglycerides had a germicidal, fungicidal and deodorizing effect. Finally, De Villez, U.S. Pat. Nos. 4,451,480 and 4,591,602, discloses use of ozonides of certain fatty acids, including olive oil, sesame oil, jojoba oil, castor oil and peanut oil, for external use as antimicrobial agents, particularly in the treatment of acne. None of the prior art discloses or even suggests an insecticidal or repellent activity of any type of ozonide structure.

Prior art insecticidal compositions are well known. However, many of these compositions are excessively toxic to other organisms in the ecosystem. In addition, many of these compositions are extraordinarily long-lived, and persist within the environment to which they are applied almost indefinitely. Moreover, many insect species have evolved resistance to many of the known insecticidal compositions. A need exists for a relatively non-toxic, shorter-lived, effective insecticidal composition.

Treatment for external insect infestations of a mammal, such as lice or crabs, often involves topical application of harsh toxic insecticidal compositions to skin or scalp. Irritation often develops, and adverse health effects from long-term use are also known. A need exists for a non-irritating, effective composition for treating such infestations without long-term adverse health effects.

Repellent compositions are also well known in the prior art. Prior art repellent compositions exist for topical application to a mammal, as well as to repel insects from entering a dwelling or other area. However, the safety of many of the topical compositions has been questioned. Moreover, many of the topical compositions are of limited effectiveness, especially in areas of severe infestation with insects. A need exists for a safe, effective topical repellent composition for a mammal. Repellent compositions for the prevention of entry of insects are similarly ineffective. Many of the known such repellent compositions also are not safe for use in enclosed spaces due to their high toxicity, especially where children and pets may come into contact with them. A need exists for a relatively non-toxic, effective repellent composition.

Insect infestations of trees and other woody plants destroy millions of ornamental and agricultural trees every year. Current treatments are only partially successful, and may render the current crop of agricultural products inedible due to their persistent toxicity. Thus, a need exists for a relatively non-persistent, effective treatment for insect infestations of trees and woody shrubs.

Dutch Elm Disease has destroyed millions of elm trees across the United States. The disease is caused by a fungus which is spread from tree to tree by a particular species of insects attracted to the elms. Current methods of prophylaxis have had only limited success. A need exists for an effective prophylaxis for this destructive plant disease.

SUMMARY OF THE INVENTION

According to the invention, there are provided novel insecticidal and repellent compositions containing ozonides of unsaturated hydrocarbons. The invention also provides methods of use for said compositions.

We have discovered surprising insecticidal and repellent properties in compositions of ozonides of unsaturated hydrocarbons.

Preferably, the compositions of the present invention are in a form comprising a concentration of the active compound which is effective insecticidally or as a repellent. In one preferred embodiment of the invention, the insecticidal or repellent composition is comprised of active ingredient without fillers or excipients. However, other preferred embodiments may contain suitable diluents or fillers. Such diluents or fillers are preferably hydrophobic solvents because water and other hydrophilic solvents may lead to decomposition of the active compound.

In one preferred embodiment, the composition is comprised of active ozonide in a suitable vehicle for injection into trees and other woody shrubs. In another preferred embodiment, the composition is suitable for aerial application to crops. In another preferred embodiment, the composition is included in aerosol cans or pump sprays for home use. In another preferred embodiment, the composition is in the form of a thick sticky substance which may be painted around trees, doors, or windows. In still another embodiment, the composition is comprised of active ingredient in a composition suitable for topical application to human skin. This embodiment includes aerosol sprays, creams, ointments, and waxy sticks.

DETAILED DESCRIPTION OF THE INVENTION

Ozonides of unsaturated hydrocarbons may be prepared from virtually any hydrocarbon molecule containing sites of unsaturation. While not limiting the scope of the invention, examples of unsaturated hydrocarbons which may prove especially effective, when ozonized and used in the compositions of the preferred embodiment, include terpenes and unsaturated fatty acids derived from plant and animal sources. Other examples of suitable unsaturated hydrocarbons include natural and synthetic steroids, alkenes and their substituted derivatives, and other naturally or synthetically unsaturated hydrocarbons derived primarily from petroleum.

In the ozonide synthesis, ozone is passed through the unsaturated hydrocarbon under conditions that provide for intimate contact between the hydrocarbon starting material and the ozone, such as thin film procedures, sparging, gas entrainment procedures, and the like. On a small scale, for example, the hydrocarbon is placed in a vented vessel, and ozone is sparged through the material until the reaction is complete. The ozone may advantageously be generated with any of the commercially-available ozone generators. Such devices include corona discharge tubes through which oxygen gas may be passed. For example, pure oxygen gas passing through an ozone generator will typically leave the device as from 2% to 6% $O_3$ (ozone), with the remainder $O_2$. This ozone mixture may then be sparged through the hydrocarbon at ambient temperature and pressure until the reaction is complete. Completion may be judged by analyzing the gas exiting the ozonation chamber for ozone. (This may be done by passing the exit gas through aqueous potassium iodide and determining whether iodine gas is liberated, or by any other conventional technique.) Alternatively, the reaction may be followed by observing the weight gain of the material undergoing the reaction, by observing changes in physical characteristics (such as conversion from a liquid form to a soft paste), or by simply calculating the quantity of ozone needed to fully ozonate the material and stopping the reaction when a slight excess of ozone has passed through the reaction chamber. Because the reaction is exothermic, its progress may also be followed by monitoring the heat evolved by the reaction medium, and stopping the flow of ozone when the mixture ceases to generate heat.

When the hydrocarbon is normally a solid, such as β-carotene, it may be solubilized in any suitable saturated nonaqueous solvent system prior to ozonation. With all of the ozonides, it is desirable to exclude water, lower alcohols, nucleophilic peroxides, and proton donors from the reaction mixture and from the final composition, in order to prevent premature hydrolysis of the trioxolane ring.

Other suitable ozonation procedures may be used, such as the procedures disclosed in U.S. Pat. Nos. 2,083,572, 3,504,038, and 4,451,480.

EXAMPLE 1

PREPARATION OF SQUALENE OZONIDE

The ozonide of squalene is prepared by combining a solution of 10 g squalene with 100 ml hexane. Ozone gas (4% in oxygen, from a corona discharge ozone generator), is bubbled through this solution via a glass sparger at the rate of 5000 cc/min. The reaction is exothermic, and the reaction temperature is kept within the range of 0° C. to 35° C., preferably 20° C. to 25° C., and more preferably, 22° C. to 24° C., using a cool water bath. The resulting product is the ozonide of squalene, a thick tarry material with a 98% weight gain over squalene.

EXAMPLE 2

PREPARATION OF STYRENE OZONIDE

The ozonide of styrene is prepared by bubbling ozone (4% in oxygen, from a corona discharge ozone generator) through 100 ml neat styrene via a glass sparger. The reaction is exothermic, and the reaction temperature is kept within the range of 0° C. to 35° C., preferably 20° C. to 25° C., and more preferably, 22° C. to 24° C., using a cool water bath. The resulting product is the ozonide of styrene with a boiling point of 55° C.

EXAMPLE 3

PREPARATION OF CHOLESTEROL OZONIDE

The ozonide of cholesterol is prepared by bubbling ozone (4% in oxygen, from a corona discharge ozone generator) through 5 ml neat cholesterol at the rate of 5000 cc/min. The reaction mixture is cooled in a water bath, and after 20 minutes, the evolution of heat ceases, indicating completion of the ozonation process. The resulting material has no odor, and is soluble in polyethylene glycol, isopropyl myristate, and mineral oil.

We have discovered that application of compositions containing certain particular ozonides of hydrocarbons to a surface creates a repellent barrier across which crawling insects, such as ants and cockroaches, will not cross. While not limiting the scope of the invention, examples of ozonized hydrocarbons which are particularly effective in this regard are squalene ozonide, linalool ozonide, and linalyl acetate ozonide. In this regard, we have discovered that application of such a repellent barrier composition around doors, windows, and other openings into a dwelling creates a barrier to entry of such a dwelling by crawling insects. We have further discovered in this regard, that application of such a repellent barrier composition in a ring around the base of a tree will prevent crawling insects from climbing into the branches of such a tree where the fruit and other edible parts are located. In one preferred embodiment of the present invention, ozonides of hydrocarbons are formulated into repellent barrier compositions suitable for application to a surface. These repellent preparations include one or more hydrocarbon ozonides and may further include other active ingredients. In addition, any of the well-known carriers or excipients may be combined with the active compounds in a well-known manner. Suitable diluents include, for example, polyethylene glycol (m.w. 150–1500), isopropyl myristate, and mineral oil. Conventional coloring, fragrance and preserving agents may also be provided.

In addition, the use of ozonides as repellent barriers in accordance with the present invention appears to have significant unexpected properties that are different in kind or quality from those of repellent barriers disclosed in the prior art.

While the compounds may be used neat (and, indeed, some of them form suitably thick tarry materials for application to a tree in a ring, e.g., squalene ozonide), preferably, the compositions include a hydrophobic solvent to protect the active ingredient from decomposition through contact with precipitation or other water. The effective concentrations of active ingredient in repellent barrier compositions appears to be quite low, suggesting that the compounds have unexpectedly high efficacy. The effective concentration for most repellent barrier applications can be as little as 1% by weight. The compositions more preferably contain from about 1% or 10% to about 90% or 100% by weight active ingredient.

EXAMPLE 4

A REPELLENT BARRIER COMPOSITION EFFECTIVE AGAINST ANTS 50 mg/ml: Ozonide of linalool
10% (w/v): Toluol
balance: Petroleum distillates Application of the above mentioned repellent barrier compositions to an already infested area is insecticidal against the insects causing the infestation. It is believed that certain particular ozonized hydrocarbons may be formulated into effective insecticidal compositions. In a preferred embodiment of the invention, hydrocarbon ozonides are formulated into insecticidal compositions for use in any of the well-known delivery systems for home, agricultural, or commercial use, including aerosol and pump sprays, aerial application, and inclusion in poisoned bait. Because water is not a suitable diluent, compositions for home use preferably come in ready-to-use form. In a preferred embodiment, suitable diluents may be added by the user in compositions for agricultural or commercial use. Such suitable diluents include PEG, isopropyl myristate, and any of the well-known petroleum derived diluents used with insecticides.

It is believed that insecticidal compositions when formulated in the manner of a preferred embodiment have considerably less long-term toxicity to the ecosystem than do prior art insecticidal compositions. In addition, it is believed that the insecticidal compositions when used in accordance with the preferred embodiment appear to have other significant unexpected properties that are different in kind or quality from those of insecticidal compositions disclosed in the prior art. The effective concentration of active ingredient for most of the insecticidal compositions of the present invention can be as little as 0.1% by weight. The compositions more preferably contain from about 0.1% or 1% to about 20% or 50% by weight active ingredient.

EXAMPLE 5

AN INSECTICIDAL COMPOSITION EFFECTIVE AGAINST LOCUSTS IN AERIAL APPLICATION

10% (w.v): Ozonide of styrene from Example 2
balance: mineral oil

We believe that topical application of ozonized hydrocarbons is also effective in the repellance of insects from the skin of a mammal. In one preferred embodiment of the present invention, ozonides of hydrocarbons are formulated into topical repellent preparations. These repellent preparations include one or more hydrocarbon ozonides and may further include other active ingredients. In addition, any of the well-known pharmaceutically-acceptable carriers or excipients may be combined with the active compounds in a well-known manner. Suitable diluents include, for example, polyethylene glycol (m.w. 150–1500, preferably about 600), isopropyl myristate, and mineral oil. The repellent composition may be in any form suitable for topical use, such as an ointment, gel, cream, aerosol or non-aerosol spray, or stick. Conventional coloring, fragrance and preserving agents may also be provided.

In addition, the use of ozonides as repellents in accordance with the present invention appears to have significant unexpected properties that are different in kind or quality from those of repellents disclosed in the prior art.

While the compounds may be used neat (and, indeed, some of them form pharmaceutically elegant creams or ointments, e.g., jojoba oil ozonide, linalyl ozonide and linalool ozonide), preferably, the compositions include a hydrophobic solvent to protect the active ingredient from too-rapid decomposition through contact with perspiration. The effective concentrations of active ingredient in repellent compositions appears to be quite low, suggesting that the compounds have unexpectedly high efficacy. The effective concentration for most topical applications can be as little as 0.01%, by weight. The compositions more preferably contain from about 0.5% or 1% to about 10% or 20% by weight active ingredient.

EXAMPLE 6

A TOPICAL OIL EFFECTIVE AS AN INSECT REPELLENT

2% w/v: Ozonide of linalyl acetate
Balance: Mineral oil

EXAMPLE 7

A TOPICAL GEL EFFECTIVE AS AN INSECT REPELLENT

1% w/v: Ozonide of cholesterol from Example 3
60% w/v: Carbomer 934
1% w/v: Disodium edetate
10% w/v: Glycerin
Balance: Polyethylene glycol m.w. 400

EXAMPLE 8

A TOPICAL INSECT REPELLENT STICK 2.5% w/v: Ozonide of linalool
48% w/v: Petrolatum
Balance: Bee's wax

EXAMPLE 9

TEST FOR EFFICACY OF REPELLANCE OF INSECTS

The composition of Example 6 is applied to the exposed arms and legs of 10 adult volunteers. Mineral oil without active ingredient is applied to 10 other adult volunteers as a control group. Each group is separately placed for five minutes in a room containing approximately 50 mosquitos of various species per cubic foot. Volunteers in the control group receive significantly more bites than those in the treated group.

It is believed that injection of a composition containing certain particular ozonized hydrocarbons into a tree or other woody plant infested with insects will destroy the infestation and allow the plant to recover. It is further believed, that injection of such a composition into a healthy plant will prevent infestations from occurring, due to the repellent properties of the composition. In this regard, it is believed that injection of American Elm trees with such a composition containing active ozonized hydrocarbons will convey a degree of protection against Dutch Elm Disease by decreasing attack by the insect bearing the fungus which causes the disease. In a preferred embodiment of the present invention, ozonides of hydrocarbons are formulated into emulsions suitable for injection into the woody parts of trees and shrubs. These injectable compositions include one or more hydrocarbon ozonides and may further include other active ingredients. In addition, any of the well-known carriers or excipients may be combined with the active compounds in a well-known manner. Suitable diluents include, for example, polyethylene glycol, isopropyl myristate, and lecithin.

EXAMPLE 10

AN INJECTABLE COMPOSITION FOR FRUIT FLY INFESTATIONS OF FRUIT TREES 25 mg/ml: ozonide of linalyl acetate
balance: Polyethylene glycol m.w. 200

I claim:

1. A repellent composition for repelling insects from a surface, comprising an ozonized unsaturated hydrocarbon in a concentration effective to repel insects and a carrier, excipient, or diluent suitable for application to the surface.

2. A composition of claim 1, wherein said hydrocarbon is a terpene.

3. A composition of claim 2, wherein said terpene is selected from the group consisting of linalool and geraniol.

4. A composition of claim 1, wherein said hydrocarbon is a steroid.

5. A composition of claim 1, comprising said ozonide of a hydrocarbon without carriers or diluents.

6. A composition of claim 1, wherein said composition is suitable for aerial application to crops.

7. A composition of claim 1, wherein said composition is in a form of an injectable emulsion, suitable for injection into the woody parts of a tree or shrub.

8. A method of treating insect infestations in a tree or shrub through injection of a composition of claim 7.

9. A method of preventing insect infestations in a tree or shrub through injection of a composition of claim 7.

10. A method of preventing or treating insect infestations of crops through aerial application of a composition of claim 1.

11. A method of preventing the ingress of insects into an area through the application of a composition of claim 1.

12. The method of claim 11, wherein said application consists of application of said composition to doors, windows and other openings of a building.

13. The method of preventing infestations of a tree by painting a ring of a composition of claim 1 around the trunk of said tree.

14. A repellent composition of claim 1, wherein the surface is the skin of a mammal, and wherein said carrier, excipient, or diluent is pharmaceutically acceptable for topical application.

15. A method of repelling insects from a mammal's skin through the topical application of a composition of claim 14.

16. The method of claim 15, wherein said composition is in the form of a spray.

17. The method of claim 15, wherein said composition is in the form of a stick.

18. The method of claim 15, wherein said composition is in the form of a repellent oil or ointment.

* * * * *